(12) United States Patent
Duefert et al.

(10) Patent No.: US 10,308,623 B2
(45) Date of Patent: Jun. 4, 2019

(54) METHOD FOR PRODUCING TETRAHYDROFURANE, 1,4-BUTANEDIOL OR GAMMA-BUTYROLACTONE

(71) Applicant: BASF SE, Ludwigshafen (DE)

(72) Inventors: Alexander Duefert, Ludwigshafen (DE); Rolf Pinkos, Bad Duerkheim (DE); Wolf-Steffen Weissker, Lambsheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/541,960

(22) PCT Filed: Jan. 8, 2016

(86) PCT No.: PCT/EP2016/050245
§ 371 (c)(1),
(2) Date: Jul. 6, 2017

(87) PCT Pub. No.: WO2016/110556
PCT Pub. Date: Jul. 14, 2016

(65) Prior Publication Data
US 2018/0002303 A1    Jan. 4, 2018

(30) Foreign Application Priority Data
Jan. 9, 2015 (EP) ..................... 15150615

(51) Int. Cl.
| | | |
|---|---|---|
| *C07D 307/08* | (2006.01) |
| *C07C 29/149* | (2006.01) |
| *C07D 307/33* | (2006.01) |
| *C12P 7/18* | (2006.01) |
| *C12P 17/04* | (2006.01) |

(52) U.S. Cl.
CPC .......... *C07D 307/08* (2013.01); *C07C 29/149* (2013.01); *C07D 307/33* (2013.01); *C12P 7/18* (2013.01); *C12P 17/04* (2013.01)

(58) Field of Classification Search
None
See application file for complete search history.

(56) References Cited

U.S. PATENT DOCUMENTS 8,673,598 B2 * 3/2014 Schroder .................. C12N 1/32
435/121

FOREIGN PATENT DOCUMENTS

| | | |
|---|---|---|
| DE | 1141282 B | 12/1962 |
| DE | 3726805 A1 | 2/1989 |
| DE | 10009817 A1 | 9/2001 |
| DE | 10061556 A1 | 6/2002 |
| EP | 2476674 A2 | 7/2012 |
| FR | 1386278 A | 1/1965 |
| JP | 20031133171 A | 4/2003 |
| WO | 03006446 A1 | 1/2003 |
| WO | 2009024294 A1 | 2/2009 |
| WO | 2010092155 A1 | 8/2010 |
| WO | 2015058990 A1 | 4/2015 |
| WO | 2016008904 A1 | 1/2016 |
| WO | 2016110520 A1 | 7/2016 |

OTHER PUBLICATIONS

Sakakura et al., "Brønsted Base-Assisted Boronic Acid Catalysis for the Dehydrative Intramolecular Condensation of Dicarboxylic Acids", Organic Letters, 2011, 13(5), pp. 892-895.

* cited by examiner

*Primary Examiner* — Heidi Reese
(74) *Attorney, Agent, or Firm* — Armstrong Teasdale LLP

(57) ABSTRACT

Processes for preparing tetrahydrofuran and/or butane-1,4-diol and/or gamma-butyrolactone are provided, including a process for preparing tetrahydrofuran (THF) from succinic acid that has been obtained by conversion of biomass, by conversion of the succinic acid to succinic anhydride, and hydrogenation of the succinic anhydride, with removal of certain secondary components.

15 Claims, No Drawings

METHOD FOR PRODUCING TETRAHYDROFURANE, 1,4-BUTANEDIOL OR GAMMA-BUTYROLACTONE

CROSS-REFERENCE TO RELATED APPLICATIONS

This application is a U.S. National Phase Application of PCT/EP2016/050245, filed Jan. 8, 2016, which claims the benefit of priority to European Patent Application No. 15150615.1, filed Jan. 9, 2015, the entire contents of which are hereby incorporated by reference herein.

BACKGROUND

The invention relates to a process for preparing tetrahydrofuran and/or butane-1,4-diol and/or gamma-butyrolactone, especially to a process for preparing tetrahydrofuran (THF) from succinic acid which has been obtained by conversion of biomass, by conversion of the succinic acid to succinic anhydride and hydrogenation of the succinic anhydride, with removal of troublesome secondary components.

The preparation of THF by hydrogenation of carboxylic acid derivatives such as maleic anhydride, maleic acid, maleic esters, succinic anhydride, succinic acid and succinic diesters is known per se. For instance, DE 100 61 556 A1 describes the hydrogenation of dicarboxylic acids and derivatives thereof over Cu catalysts in the gas phase. The emphasis is the hydrogenation of maleic anhydride prepared by gas phase oxidation, for example, of butane. WO 2003 006 446 gives a similar description, the emphasis here being on the hydrogenation of the diesters. None of the documents mentions how THF is prepared proceeding from succinic acid prepared by fermentation.

EP 2 476 674 A2 describes how cyclic compounds (lactones and ethers) are prepared proceeding from $C_4$-$C_6$ carboxylic acids or esters thereof. There is explicit mention of the use of biomass-based acids or esters produced therefrom. Preference is given to using a catalyst which is neutral, in order that no by-products that result from dehydration are generated. There is no mention of the use of succinic anhydride. Nor is there any teaching as to how impurities present in the starting materials are removed or the influence thereof is limited to a minimum.

The preparation of succinic acid from biomass is described, for example, in WO 2010/092155 A1. In addition, this WO also describes the further processing of succinic acid or diesters thereof to obtain THF, butanediol and/or gamma-butyrolactone, the esters being obtained, for example, by reactive distillation esterification of diammonium succinate. Otherwise, salts of succinic acid are converted to free succinic acid by acidic ion exchangers which are then regenerated, for example, with HCl. The purification of this succinic acid thus obtained is then effected by concentration and crystallization. In example 9, the purity of the succinic acid is stated as 99.8%. There is no description of what impurities are present and how these may then effect the hydrogenations. Nor is there any mention of succinic anhydride.

The preparation of succinic anhydride from succinic acid is known per se. DE-A-1 141 282 describes the preparation of succinic anhydride by feeding liquid succinic acid into a column, wherein water is distilled off overhead and the anhydride is obtained via the bottom with a purity of 95%-97%. Nothing is said about the impurities. According to FR 1 386 278, succinic acid is dewatered by distillation, leaving the anhydride in the residue. According to *Org. Lett.* 2011, 13, 892, succinic acid is formed in a homogeneously catalyzed process with the catalyst as high boiler; the purification is effected by precipitation of the anhydride and filtration of the reaction mixture.

JP 2003 113 3171 A describes the purification of succinic anhydride by distillation, wherein the distillation of the crude succinic acid to avoid discoloration of the product the bottom temperature at reduced pressure is between 125 and 200° C. Only dilactones are described as impurities to be avoided. There is no mention of the preparation of succinic anhydride by means of succinic acid obtained from fermentative processes. In addition, no effect on downstream hydrogenation steps is detailed; instead, only discoloration of polyesters prepared with contaminated succinic anhydride is mentioned.

In contrast to products which are prepared by conventional chemical reactions, the peculiarity of products which are obtained from biomass lies in the disproportionately higher number of secondary components which can disrupt downstream applications, particularly when polymers having long chain lengths are to be formed, where monofunctional groups disrupt the formation of chains. In this present case, a main use of THF is the preparation of polytetrahydrofuran. Moreover, secondary components can have a disruptive effect on catalysts in terms of selectivity and yield of the process, but in particular have an adverse effect on the lifetime of the catalysts. Examples of these disruptive secondary components which can be harmful even in amounts below 1 ppm by weight comprise the elements N, P, S, As, Sb, Bi, Sn and halogens such as Cl, Br and I.

N-comprising compounds, particularly when they have basic properties, can occupy acidic centers on catalysts and hence destroy desirable properties. More particularly, the nitrogen-comprising compounds are harmful when they pass through a hydrogenation step, since it is only this that causes many of them to become basic compounds. This can then hinder the hydrogenation step or downstream processes. Here, the polymerization of THF is again adversely affected, since it is conducted in the presence of acidic catalysts. Especially in the case of hydrogenation of succinic anhydride in the presence of N-containing catalysts, especially of ammonia or those that can release it, it is easy for pyrrolidine to form, which hinders the hydrogenation process and, because of its boiling point being similar to that of THF, is separable therefrom only with difficulty, and disrupts the polymerization at a later stage.

Compounds comprising P, S, As, Sb, Bi, Sn or halogens such as Cl, Br and I are undesirable, since some are not just toxic to the environment but can also poison hydrogenation catalysts. Many of these compounds are volatile, and so they can partly withstand distillative purifying processes or get into the stream to be hydrogenated in gas phase processes.

In fermentative processes for preparing succinic acid, acids formed by way of example are not just succinic acid but also a number of other acids such as formic acid, acetic acid, propionic acid and butyric acid. Because of their acid strength, these are capable of damaging catalysts.

DETAILED DESCRIPTION

It is an object of the present invention to provide a process for preparing tetrahydrofuran and/or butane-1,4-diol and/or gamma-butyrolactone, preferably tetrahydrofuran (THF), from succinic acid prepared by fermentation, which avoids the disadvantages of known processes and reports the desired products in high yield and purity. The hydrogenation catalyst used in the necessary hydrogenation step is to have a long lifetime. In addition, the process is to be performable with minimum complexity.

The object is achieved by a process for preparing tetrahydrofuran and/or butane-1,4-diol and/or gamma-butyrolactone, comprising the steps of a) fermentative preparation of succinic acid,
b) conversion of the succinic acid from step a) with elimination of water and removal of water to succinic anhydride,
c) conversion of the succinic anhydride from step b) to the gas phase,
d) removal of sulfur compounds from the succinic anhydride by passing the succinic anhydride from step c) through a fixed guard bed which absorbs the sulfur compounds,
e) hydrogenation of the gaseous succinic anhydride from step d) in the presence of free hydrogen over a metallic catalyst to give tetrahydrofuran and/or butane-1,4-diol and/or gamma-butyrolactone.

It has been found in accordance with the invention that, in the preparation of tetrahydrofuran, butane-1,4-diol and/or gamma-butyrolactone proceeding from succinic acid, the hydrogenation can be conducted with a long catalyst lifetime if succinic acid prepared by fermentation is purified via succinic anhydride, and sulfur compounds are removed from the succinic anhydride with the aid of a fixed guard bed.

Butane-1,4-diol can be reacted further at a later stage with dicarboxylic acids or diisocyanates.

As well as sulfur compounds, further disruptive compounds comprising P, As, Sb, Bi, Sn or halogens such as Cl, Br or I are preferably also ab- and/or absorbed by the guard bed, such that they do not get into the stream to be hydrogenated which is contacted with the hydrogenation catalyst.

Step a)

Fermentation refers in biology to a form of enzymatic conversion of organic substances. Fermentation is employed in many biotechnological production methods. This is accomplished, for example, by addition of the enzymes required or by addition of bacterial, fungal or other biological cell cultures which conduct fermentation in the course of their enzyme-catalyzed metabolism.

This fermentation broth preferably comprises enzymes, bacteria, fungi and/or other biological cell cultures. In addition, the fermentation broth comprises biomass.

Biomass is understood, for example, to mean substances which either occur directly in nature, such as starch, cellulose or sugars, or are derived therefrom, such as glycerol, and sugars formed by cleavage, such as glucose, sucrose, etc., and $CO_2$. In this context, reference is made to WO 2010/092155 A1 and the raw material sources mentioned therein. The preferred preparation of succinic acid proceeds via fermentation.

The microorganisms required may already be present on starting materials. However, preference is given to adding pure single-cell cultures in fermentation processes of the invention, in order to better control the fermentation and rule out unwanted by-products. Therefore, the sterile mode of operation of the reactor is important.

The main field of use of fermentation is biotechnology for production of a wide variety of different fermentation products, such as bioethanol, amino acids, organic acids such as lactic acid, citric acid and acetic acid, enzymes such as phytase, antibiotics and other pharmaceutical products, biomonomers and biopolymers.

For a more detailed description of fermentation, reference may be made to WO 2009/024294 and WO 2010/092155.

The reactors of the invention may replace stirred fermenters and also bubble columns. Fermentation methods are described in general terms in Chmiel; Bioprozesstechnik: Einführung in die Bioverfahrenstechnik [Bioprocess Technology: Introduction into Biochemical Engineering], vol. 1, and in Chmiel, Hammes and Bailey; Biochemical Engineering. These may be batch methods, fed batch methods, repeated fed batch methods or continuous fermentation methods with or without recycling of the biomass. In these cases, the yield is often increased with a through-flow of air, oxygen, carbon monoxide, carbon dioxide, ammonia, methane, hydrogen, nitrogen or suitable gas mixtures.

The fermentation broth can also be pretreated; for example, the biomass can be removed from the fermentation broth. For this purpose, it is possible, for example, to employ methods such as filtration, sedimentation and flotation. The biomass can be removed by centrifuging, separators, decanters, filters or deflotation apparatuses. In addition, the biomass can be washed, for example in the form of a diafiltration, in order to maximize the product yield. The fermentation broth can additionally be concentrated, for example by evaporative concentration under suitable conditions. Suitable evaporators are known.

The fermentation can be used in accordance with the invention especially for preparation of succinic acid or salts or derivatives thereof. Suitable methods are described, for example, in WO 2010/092155 on pages 17 to 19 and in the examples.

The fermentation, for example according to WO 2010/092155 A1, is generally followed by the separation of the biomass from the product, for example by filtration. This removes solids, especially cells. The product of the fermentation may be succinic acid directly, but the highest yields are currently achieved when the succinic acid is obtained as a salt, in order that the fermentation can proceed within a pH range between 6 and 8. These salts are, for example, mono- and disalts of succinic acid with ammonia or amines, and of the alkali metals or alkaline earth metals. Mixtures are also possible. Succinic acid can be obtained from these salts by acidifying. This can be accomplished, for example, with the aid of the acidic ion exchangers which are subsequently regenerated again, generally with mineral acids such as hydrochloric acid or sulfuric acid, or by acidification with acids such as formic acid, hydrochloric acid, sulfuric acid, carbonic acid or phosphoric acid. Likewise possible is what is called electrodialysis, in which aqueous succinic acid solution and, according to the counterion of succinic acid, for example, alkali metal or alkaline earth metal hydroxides are formed by means of current and membranes, and the latter can be recycled into the fermentation.

Depending on the impurities obtained in the preparation process and the workup to give the purified succinic acid, the latter may include compounds comprising P, S, As, Sb, Bi, Sn or halogens such as Cl, Br and I.

Since the fermentation is conducted in water, succinic acid or salts thereof are usually obtained in the form of aqueous solutions. The acidification of the salts to obtain free succinic acid is usually likewise an aqueous process to obtain aqueous succinic acid solutions having a content of generally 1% to 15% by weight of succinic acid which, according to the concentration, may have to be temperature-controlled in order that succinic acid does not precipitate out if this is undesirable.

It is also possible, prior to the acidification of the salts, to concentrate the solutions by removal of water, for example by distillative removal or by pervaporation. Subsequently, the usually warm salt solution having a content of, for example, 10% to 60% by weight of succinic salt can be acidified at temperatures of 20-100° C. This may be followed by cooling, in order that the succinic acid precipitates out. The crystallized succinic acid is subsequently filtered out of the aqueous salt solution, for example Na or Mg salts of hydrochloric or sulfuric acid.

A first crystalline succinic acid material can be dissolved once more in water and crystallized again for further purification, but with losses of product as a result of discharges. This can be done as many times as necessary to purify the succinic acid to the desired specification, but the yield decreases with every crystallization step. In the process according to the invention, preference is given to crystallizing not more than twice, more preferably not more than once. This is also because crystallizations not only reduce the yield, but the capital costs thereof are also considerable.

The succinic acid prepared in this way generally comprises the impurities which follow, the amount of impurities decreasing with the number of purification steps, acidification having been effected with HCl below, and the % figures being % by weight or ppm by weight calculated on the basis of the particular element.

Aqueous succinic acid solution after acidification with HCl
Crystals after 1st crystallization:
Sum total of halogen calculated as chlorine 0.01% to 2%
Sulfur 0.001% to 0.1%
Nitrogen 0.001% to 0.1%
Phosphorus 0.01 to 100 ppm
Sum total of arsenic, antimony, bismuth, tin 0.01 to 20 ppm
Magnesium 0.1 to 1000 ppm
Sum total of iron, manganese, chromium, molybdenum 0.1 to 100 ppm
Calcium 0.1 to 100 ppm
Sum total of sodium, potassium 0.1 to 100 ppm
Crystals after 2nd crystallization:
Sum total of halogen calculated as chlorine 0.01 to 20 ppm
Sulfur 0.01 to 10 ppm
Nitrogen 0.01 to 10 ppm
Phosphorus 0.01 to 3 ppm
Sum total of arsenic, antimony, bismuth, tin 0.01 to 3 ppm
Magnesium 0.01 to 3 ppm
Sum total of iron, manganese, chromium, molybdenum 0.01 to 3 ppm
Calcium 0.01 to 3 ppm
Sum total of sodium, potassium 0.01 to 3 ppm According to the invention, the sulfur content, based on succinic acid, at the end of step a), is preferably in the range from 0.001% to 0.1% by weight or 0.01 to 10 ppm.

Preferably, in step a), succinic acid is prepared by fermentation from at least one carbon source and, after the biomass has been separated from the fermentation broth, is converted to the acid form by acidifying. More preferably, the succinic acid thus prepared is transferred into step b) without any further/additional purification steps.

Temperatures stated in the steps which follow, unless stated otherwise, are based on the bottoms in the particular evaporation or distillation. Pressures stated, unless stated otherwise, are based on the top of the distillation (top pressure). In the case of simple evaporations, the pressure is that in the evaporation stage.

Step b)

In the process according to the invention, succinic acid is then introduced as an aqueous solution or as a melt which may still comprise water into step b) of the invention. According to the water content, water of solution may be removed in a first step, in which case the conversion of succinic acid to the anhydride may already proceed, in which case water is again released and is then removed as well in this step. Preference is given to introducing a succinic acid solution having a concentration of 5%-50% by weight into one or more evaporation apparatuses connected in series or parallel, in which water is distilled off preferably at 100 to 250° C. (temperature measured in the bottoms) and preferably at pressures of 50 to 1000 mbar absolute. Preference is given to 150 to 220° C., particular preference to 150 to 200° C., at preferred pressures of 0.1 to 0.5 bar absolute, more preferably at 0.15 to 0.3 bar absolute. For optimal energy exploitation, the evaporation devices may optionally be coupled to other plant units in an integrated system. A column may be placed atop the evaporation apparatus to prevent the loss of succinic acid or anhydride by reflux. The evaporator apparatus may, for example, be a simple tank which can be stirred and/or pumped in circulation. Likewise possible is a falling-film, thin-film, natural-circulation, forced-circulation or helical-tube evaporator. The bottom product in which succinic anhydride that has already formed is present and which has a water content of preferably 0.01% to 30% by weight, preferably 0.05% to 15% by weight, more preferably 0.1% to 10% by weight can then be transferred as such into step c), or it can be converted further and concentrated in a further distillation unit.

Step c)

In step c), the succinic anhydride from step b) is converted to the gas phase.

Preferably, step c) can be conducted in at least one distillation apparatus at a top pressure in the range from 0.02 to 2 bar and a bottom temperature in the range from 100 to 300° C. with removal of high boilers via the bottom. Preferably, in this embodiment, step c) is conducted at lower pressure than step b) and, in step c), water and any low boilers are removed via the top, and gaseous succinic anhydride is obtained via a side draw.

Alternatively, step b) and step c) may be combined and conducted in at least one distillation apparatus at a top pressure in the range from 0.02 to 2 bar and a bottom temperature in the range from 100 to 300° C., preferably see below with removal of high boilers via the bottom, removal of water via the top and recovery of gaseous succinic anhydride via a side draw. The individual process alternatives are elucidated in detail hereinafter.

Together with the water, in this step, harmful carboxylic acids such as formic acid and acetic acid in particular are preferably removed, in order that they cannot damage the catalyst later as a result of corrosion thereof.

In this further distillation unit (or a plurality of distillation units connected in series or parallel), succinic anhydride which may still comprise succinic acid is purified further or prepared. What is crucial here is that succinic anhydride is converted to the gas phase, in order that it can be separated preferentially from high-boiling impurities. In order that the purifying effect is at a maximum, the distillation is preferably operated with reflux. Preferably, the reflux volume based on the amount of succinic acid/succinic anhydride added is between 0.1 and 10 parts, more preferably 0.2 to 5 parts. The high boilers are discharged via the bottom.

In this stage, there are two preferred process variants: in one variant, the high boilers are separated from gaseous succinic anhydride at 100 to 300° C., preferably 150 to 270° C., more preferably 170 to 250° C. (bottom temperatures) and (top) pressures of 0.02 to 2 bar absolute, preferably of 0.03 to 1 bar and more preferably of 0.04 to 0.5 bar. In this case, the succinic anhydride produced in gaseous form is preferably not condensed for preparation of THF and is discharged from the distillation apparatus. Subsequently, it is transferred into stage c) of the invention.

In the other variant, which comprises the connection/combination of steps c) to e) of the invention, succinic anhydride is evaporated in the presence of hydrogen, with condensation of a portion of the gaseous succinic anhydride to produce the reflux. The rest passes together with the hydrogen through the guard bed into the hydrogenation. This is generally conducted at bottom temperatures of 150 to 300° C., preferably 160 to 270° C., more preferably 180 to 250° C., at pressures (absolute) of 1 to 65 bar, preferably 2 to 30 bar, more preferably at 5 to 20 bar. In a preferred variant, the succinic anhydride is exposed to the hydrogen stream for evaporation of the succinic anhydride together with a solvent having a higher boiling point than succinic anhydride. This has the advantage that, for example, a column for driving out or stripping the anhydride can be operated more efficiently, since the column trays are wetted by the high-boiling solvent even in the case of a decreasing concentration of anhydride. This solvent is preferably circulated by the stripping column. Examples of this solvent, which should preferably be inert toward succinic anhydride and hydrogen, are phthalates or terephthalates based on $C_4$ to $C_{15}$ alcohols, for example dibutyl phthalate, correspondingly ring-hydrogenated phthalates or terephthalates, hydrocarbons, ethers based on ethylene oxide and/or propylene oxide, and the like.

To increase the yield, the bottom stream comprising succinic anhydride can be recycled wholly or at least partly into one or more preceding stages. However, particularly in the case of comparatively long-running processes for preparation of industrial product volumes of THF, a discharge to avoid accumulations is advantageous. It is therefore preferable to work up this discharge stream further in a further distillation unit. Preference is given here to using a thin-film evaporator in which succinic anhydride is distilled off overhead and is then recycled into one of the preceding stages. The high boiler stream is discharged. The evaporation is conducted at preferably 100 to 300° C., more preferably 150 to 270° C., especially preferably at 180-250° C., and pressures of preferably 1 to 200 mbar absolute, preferably between 3 and 100 mbar, more preferably at 5 to 50 mbar.

In order to remove harmful, basic N-containing compounds in step c) of the invention, it is preferable to convert the basic compounds to high-boiling substances. These basic N-containing compounds may, for example, be ammonia, aliphatic amines, amino acids, etc. In order to prevent these from being converted to the gas phase together with succinic anhydride, it is advantageous to convert them to high-boiling compounds. This can be done, for example, by working in the presence of an acid which forms high-boiling salts together with the basic compounds. Examples of these are salts of high-boiling carboxylic acids such as adipic acid, acidic amino acids, sulfonic acids such as dodecylbenzenesulfonic acid, methanesulfonic acid, mineral acids such as phosphoric acid, sulfuric acid, or heteropolyacids such as tungstophosphoric acid. Preference is given to adding 1 to 1.5 molar equivalents of acid per equivalent of basic compound. A further preferred option, optionally in addition to salt formation, is the chemical conversion of basic N-containing compounds to high-boiling compounds, for example the formation of amides. For this purpose, they are converted, for example, to ammonium sulfonates or carboxylates with residence times of 0.1 to 2 h and temperatures of 150-300° C. This can proceed, for example, in the bottoms of the evaporation units. Suitable co-reactants are, for example, sulfonic acids or carboxylic acids as described above. If basic N-containing components are not very substantially removed prior to the hydrogenation, it has to be expected that, in some cases, the acidic catalyst centers needed for the preparation of THF will be gradually neutralized and the yield of THF will be reduced as a result.

Step e)

In step e) of the invention, gaseous succinic anhydride is fed to a gas phase hydrogenation together with hydrogen. The molar ratio of hydrogen to succinic anhydride here is preferably 20-300:1, preferably 30-250:1, more preferably 50-200:1. The pressures (in absolute terms) are preferably 1 to 65 bar, preferably 2 to 30 bar, especially preferably 5 to 20 bar. The temperatures are preferably 150 to 350° C., more preferably 170 to 320° C., especially preferably 200 to 300° C.

The heterogeneous catalysts utilized for hydrogenation have, as hydrogenation metal, preferably at least one of the elements selected from Ru, Re, Co and Cu. Preferred catalysts comprise at least Cu. The percentage by weight of the hydrogenation metal in the total weight of the catalyst (calculated as the element) is preferably between 0.5% and 80%. In the case of Cu, the preferred proportion is between 10% and 80%, more preferably between 25% and 65%.

The hydrogenation metals have preferably been applied to a support system. Suitable supports preferably have acidic centers and preferably comprise oxides based on B, Al, Si, Ti, Zr, La, Ce, Cr, or carbon, for example in the form of activated carbon. An example of a further support not in oxidic form is SiC.

The preparation of the catalysts is achieved, for example, by impregnation of active metal precursors, for example Cu salt solutions, on the supports. Also suitable are precipitated catalysts in which the active components are precipitated onto a support or are precipitated from their dissolved precursors together with the support material. After the catalyst material has been dried and optionally calcined, the catalyst is preferably activated with hydrogen prior to commencement of the hydrogenation.

Particularly preferred catalysts comprise, in addition to Cu, aluminum oxide as well.

The heterogeneous catalysts are generally shaped bodies having an average particle size exceeding one millimeter. Preference is given to using extrudates, tablets, star-shaped extrudates, trilobes, hollow bodies, etc.

Useful reactors for the hydrogenation include the types known to those skilled in the art. Examples of these are shaft reactors, shell and tube reactors, fluidized bed reactors, etc. Hydrogenation may be effected in one reactor or in a plurality of reactors arranged in parallel or in series, including two or more types combined with one another. The conversion of succinic anhydride at the end of the reactors is preferably >95%, preferably >99%, more preferably >99.9%. Downstream of the reactor, the product-bearing gas stream is preferably cooled to below 60° C. for condensation of THF. Preference is given to below 40° C., particular preference to below 20° C. This can also proceed in two or more stages, in which case the temperature decreases along the gas stream through the use of two or more coolers. Preference is given to conducting the hydrogenation with cycle gas. For this purpose, the gas stream which has been very substantially freed of the product is recycled through a cycle gas compressor into the reaction, in which case it is preferably used for evaporating succinic anhydride. The hydrogen consumed as a result of the hydrogenation and any losses via offgas or gas dissolved in the liquid output is correspondingly replaced. When working with offgas for discharge of any inerts, for example nitrogen and argon, which are introduced together with the hydrogen, or compounds that form, for example methane or carbon dioxide, preferably less than 10%, more preferably less than 5% and especially preferably less than 3% of the amount is discharged, based on fresh hydrogen fed in.

Step d)

The upstream step d) of the invention is responsible to a crucial degree for the fact that the hydrogenation process can be operated for a very long period with high selectivity and high conversion. This is enabled by absorption of catalyst poisons which form volatile compounds and could get into the hydrogenation together with succinic anhydride and comprise, for example, the elements P, S, As, Sb, Bi, Sn or halogens such as Cl, Br and I, sulfur in particular, on a catalyst or absorber, also referred to here as guard bed.

The catalyst which is to absorb these catalyst poisons is, if possible, a catalyst that does not damage succinic anhydride but on the contrary preferably already has hydrogenating action in the direction of the desired product and, after absorbing the catalyst poisons, may have declining hydrogenation activity but does not have any decomposing action on the anhydride or via any product entrained in the cycle gas, for example THF. Preferably, the catalyst has a very sharp profile with high absorption capacity for the catalyst poisons. A sharp profile means that the catalyst poisons mentioned are absorbed in the guard bed within a spatially very narrow region and do not have broad distribution over the length of the guard bed. This makes it possible to exchange spent guard bed in a controlled manner, it being necessary to exchange only small amounts of guard bed. It is preferable that, measured by the behavior of sulfur, on attainment of at least 90% of the absorption capacity under reaction conditions, only 10% sulfur has been absorbed after a further 50 cm, preferably 40 cm and more preferably 30 cm along the hydrogenation pathway or guard bed. It should be noted here that catalysts which, as a result of the preparation process therefor, comprise sulfate, for example, can distort the measurements. In this case, it is necessary to subtract the "zero value" of sulfur correspondingly from the value which is caused by the sulfur in the hydrogenation feed.

Suitable catalysts for removal of P, S, As, Sb, Bi, Sn and halogens such as Cl, Br and I, especially sulfur, comprise, for example, Mo, Co, Ru, Re and Cu, unless they should also already have hydrogenating action, for example ZnO. Preference is given to Ru and Cu, particular preference to Cu. It is advantageous here when the content of metal which can absorb the catalyst poisons is at a maximum. Thus, the content of the for absorption of the poisonous constituent, measured as the element, is preferably greater than 10% based on the total weight of the catalyst, preferably >25%, more preferably >40%, but preferably not more than 90%, since the surface area capable of absorption otherwise becomes too small. The absorption capacity of sulfur, normalized to the metal content, is preferably between 0.5% and 10% by weight, more preferably between 1% and 10% by weight.

In a particularly preferred embodiment, the catalyst for removal of catalyst poisons comprises the same constituents as the actual hydrogenation catalyst, with use in the ideal case of the same catalyst for hydrogenation and poisoning removal to avoid confusion in the charge of the apparatuses, or additional catalyst production complexity.

The catalyst for removal of catalyst poisons is preferably used in the form of a fixed layer, for example in a shaft reactor or shell and tube reactor. This can be effected with spatial separation from the actual hydrogenation catalyst, i.e. in two apparatuses, in order to avoid an excessive number of apparatuses, but preferably in one reactor, together with the hydrogenation catalyst. Irrespective of whether only one or more than one apparatus is used, it is possible to work with a minimum amount of catalyst for removal of catalyst poisons if the catalyst is removed from time to time, if at all possible before it has become fully loaded, and replaced again. This is advisable when the process of the invention has to be shut down in any case, for example for maintenance operations.

The volume ratio of actual hydrogenation catalyst to catalyst that removes the poisons is preferably 3-200 to 1, preferably 5-100 to one, more preferably 10-50 to 1.

The catalyst for removal of poisons is preferably activated prior to use thereof with hydrogen at temperatures and under conditions analogous to the actual hydrogenation catalyst.

In this way, a lifetime of the hydrogenation catalyst of more than 6 months, preferably more than 1 year, can be achieved.

The removal of sulfur compounds and other catalyst poisons can also be effected in the liquid phase. This is advantageous when further process steps that lead to the desired products are effected in the liquid phase, for example the hydrogenation or an esterification of succinic anhydride or succinic acid to succinic diesters, for example dimethyl succinate, which is then hydrogenated in the gas phase.

The catalysts are the same as those which can also be employed in the gas phase and, if they are metallic in nature, have been activated, for example, with hydrogen beforehand. The temperatures for removal of unwanted secondary components in the liquid phase are preferably in the range of 50-250° C., preferably 70 to 230° C., more preferably 90 to 210° C.

The pressures are uncritical in principle, provided that there is no boiling. They are between 0.5 and 300 bar absolute. If metallic materials are used, the removal of the unwanted components is preferably effected in the presence of hydrogen.

Treatment with pure anhydride is also possible, or else it can be dissolved in inert solvents or in reaction products such as THF, gamma-butyrolactone or butanediol, or in methanol or in water.

Step f)

Preferably, the process also comprises the downstream step f) comprising the distillative separation of water and high boilers from the tetrahydrofuran, butane-1,4-diol and/or gamma-butyrolactone. Preferably, step f) in the preparation of tetrahydrofuran is conducted in at least three distillation columns, wherein f1) in a first distillation column high boilers are removed in the bottoms and a tetrahydrofuran/water azeotrope is obtained overhead, f2) the tetrahydrofuran/water azeotrope from step f1) is separated in a second column which is operated at a higher pressure than the first column in step f1) into a tetrahydrofuran/water azeotrope which is removed overhead and preferably recycled into step f1), and tetrahydrofuran which is obtained via the bottom, and f3) the tetrahydrofuran obtained via the bottom in step f2) is freed in a third column of high boilers which are discharged via the bottom.

Preferred embodiments of step f) are elucidated in detail below.

Step f) of the invention comprises the purification of the hydrogenation output. This comprises predominantly the two hydrogenation products THF and water, and additionally, in small amounts, based on the THF product, in molar terms, preferably less than 7% n-butanol, preferably less than 5%, preferably less than 2%, preferably less than 1% gamma-butyrolactone, and further products, but usually below 1% in molar terms based on THF, preferably below 0.5%, such as n-propanol, methanol, butyric acid, n-butyraldehyde, n-butyl methyl ether and other, quantitatively insignificant compounds. The yield of THF based on succinic anhydride used, over the entire service life of the hydrogenation catalyst, is preferably more than 90%, more preferably more than 95%, especially preferably more than 96%.

The hydrogenation output is freed of high boilers in a first column, wherein a THF/water azeotrope which may optionally also comprise n-butyraldehyde and other low boilers is removed overhead, and water, n-butanol and any gamma-butyrolactone formed via the bottom. This bottom product can be fractionated separately, in order to obtain butanol and gamma-butyrolactone, in which case the latter can be recycled into the hydrogenation. The top product is introduced into a further column which is preferably operated at higher pressure than the first column. Here, again, a THF/water azeotrope is removed overhead, but this time, because of the higher pressure, with a higher water content. This azeotrope is preferably recycled into the first column. Should methanol have formed in the hydrogenation, it can be discharged overhead in this column together with some THF, in which case the THF/water azeotrope is preferably obtained via a side draw in the rectifying section. The bottom product from the second column, virtually pure THF (<1000 ppm of water), is subsequently used as it already is, or else is "finely distilled" once again in a third column, for example for discharge of any high boilers such as n-butyraldehyde. The first column having preferably 10 to 80 and more preferably 40 to 60 theoretical plates is operated at an absolute pressure of preferably 0.5 bar to 4 bar, more preferably 1 bar to 3 bar, and the second column having preferably 10 to 70 and more preferably 40 to 60 theoretical plates at an absolute pressure of preferably 5 bar to 20 bar, more preferably 6 bar to 12 bar. The columns may have different internals, for example random packings, sheet metal packings, fabric packings or trays.

The workup of the hydrogenation output can also be effected as disclosed in DE-A-3726805 or in WO03/074507. Alternative purification concepts include, for example, the depletion of water by means of membrane filtration. It is likewise possible to remove water by means of concentrated sodium hydroxide solution of potassium hydroxide solution. According to these water removal methods, the THF is preferably purified further in at least one column.

Described above are preferred process variants in relation to the preparation of tetrahydrofuran (THF).

If butane-1,4-diol is the product of choice, in a first distillation step, water and by-products such as alcohols, e.g. n-butanol, n-propanol and THF, are distilled out of the butanediol. In a second step, the butanediol is purified further by introducing it, for example, into a column having a side draw and removing lower-boiling components than butanediol overhead, such as gamma-butyrolactone, obtaining butanediol via a side stream and discharging high boilers via the bottom. High boilers and gamma-butyrolactone can be at least partly discharged back into the hydrogenation, for example to an extent of more than 50%. Rather than one column having a side draw, it is also possible to use two separate columns, in which case butanediol is obtained as a pure product overhead in the second column.

If gamma-butyrolactone is the product, the distillative purification is guided by the same plan as for butanediol.

The invention is elucidated in detail by the examples which follow.

EXAMPLES

Example 1

Obtaining Succinic Ahydride (SA)

A crude fermentation output obtained according to WO 2010/092155 A1, example 6, after removal of the biomass, was acidified by filtration with HCl up to a pH of 3. This mixture was pumped continuously into a delay vessel having pumped circulation and a column on top. After a mean residence time of about 4 hours, water was then distilled off at 200 mbar and bottom temperature 180° C. The liquid bottoms at about 180° C., which comprised high boilers, SA and less than 5% free succinic acid, were introduced continuously into a column having a side draw in the rectifying section and distilled at a top pressure of 50 mbar and bottom temperatures of about 180° C. Essentially water was removed overhead, which comprised a content of 2 ppm by weight of N, and SA was discharged via the side draw and the high boilers via the bottom. In the high boilers were 0.03% by weight of N, 0.02% by weight of S. In this way, it was possible to obtain SA, based on succinic acid in the fermentation output, with about a 97% yield. The SA had a sulfur content of 5 ppm by weight.

Example 2a

Hydrogenations to THF

The apparatus used in the examples consisted of a trace-heated feed section with reservoir vessel and pump, an evaporator filled with glass rings, a tubular reactor having length 3 m and internal diameter 2.7 cm and an external oil-heated or cooled jacket and an internal thermocouple tube, a water-cooled first separator, a second separator cooled to 6° C. and a cycle gas blower, and fresh gas and offgas devices. For evaporation of succinic anhydride, the succinic anhydride (SA), the cycle gas and the fresh hydrogen were passed into the evaporator. The molar ratio of fresh hydrogen to SA was 2.1 to 1, and the excess gas was discharged as offgas. The molar ratio of cycle gas to SA was about 100 to 1.

Comparative Example 2b

The reactor was charged with 1 liter of a CuO (50% by weight)/$Al_2O_3$ catalyst (2.5 mm extrudates). Introduced above the catalyst were 100 mL of glass beads as inert bed. After inertization with nitrogen, the catalyst was activated with a nitrogen/hydrogen mixture at standard pressure. (The gas stream is adjusted to 99.5% nitrogen and 0.5% hydrogen, then the reactor is heated up to 130° C. After 2 hours, the reactor is heated up further in 5° C. stages, with each temperature setting being maintained for 30 minutes. On attainment of 180° C., the hydrogen content is increased to 1%, and after one hour to 5% again for one hour, then the hydrogen content is raised to 100%.) After the catalyst has been activated, the cycle gas blower is put into operation and the pressure in the reactor is adjusted to 9 bar absolute, and the reactor temperature to 230° C.

Subsequently, the SA feed into the reactor was started at the top. 100 g of SA/h were delivered continuously. Thereafter, the temperature in the first third of the reactor increased up to 245° C., then fell to nearly the oil heating/cooling level (about 230° C.), and then rose back up to 235° C. in the last third of the catalyst bed and then dropped again to nearly 230° C. just upstream of the end of the catalyst bed.

The liquid reaction outputs obtained in the separators were collected and combined and analyzed by gas chromatography (GC area percent). 98.3% THF and 1.5% n-butanol were found. The remainder consisted of several compounds, with each individual component not exceeding 0.05%, such as n-butyraldehyde, dibutyl ether and gamma-butyrolactone.

After a run time of 1000 h, the temperature profile in the reactor had changed in that the sites with the highest temperatures had moved backward somewhat and the reaction temperature at the end of the reactor was about 232° C., i.e. no longer reached the oil heating/cooling level. In the hydrogenation output were 95.1% THF, 1.8% n-butanol, 2.8% gamma-butyrolactone, 0.1% SA, and less than 0.05% of each of, for example, n-butyraldehyde, butyric acid, dibutyl ether and methyl butyl ether.

Shortly thereafter, the plant had to be shut down since there was a risk of blockage of the separators, probably as a result of deposition of SA.

Inventive Example 2b

Comparative example 2 was repeated, except that, above the one liter of catalyst, rather than 100 mL of glass beads, the following were introduced in this sequence: 10 mL of glass beads, 50 mL of CuO (60% by weight)/$Al_2O_3$ 3 mm tablets, and 40 mL of glass beads. The glass beads between the two Cu catalysts served to make it easier to deinstall them separately for the purpose of intended analysis. The introduction height of the 50 mL of catalyst, taking account of the internal reactor diameter and the internal tube containing the thermocouples, was about 10 cm.

After an experiment duration of 2000 h, the experiment was stopped without any significant change in the temperature profiles or the discharge composition. Thus, 98.2% THF, 1.6% n-butanol were found in the output. The remainder consisted of several compounds, with each individual component not exceeding 0.05%, such as n-butyraldehyde, dibutyl ether and gamma-butyrolactone.

By distillation in three columns, the product is purified, with discharge in the first column essentially of water, butanol and gamma-butyrolactone via the bottom, and with distillative removal in the second column which is operated at a higher pressure than the first column, of a water/THF azeotrope overhead, which is recycled into the first column, and gives anhydrous THF via the bottom, which is essentially freed of butyraldehyde (bottom product) in a third column. The resultant THF has a purity of >99.9% and can be used as such, for example, for the preparation of poly-THF. It comprises less than 1 ppm by weight of N.

The 50 mL of Cu catalyst tablets were deinstalled under protective nitrogen gas in 5 equal fractions and analyzed for their sulfur content. Compared to a sulfur content of 0.01% by weight in the unused catalyst, the sulfur contents in the first two layers were 1.5% and 0.3% by weight respectively, that in the third layer was 0.1% and those in the 4th and 5th layers were about 0.02%. Under the reaction conditions, the maximum absorption capacity for sulfur was accordingly at at least 1.5% by weight.

Hydrogenations to butane-1,4-diol

Comparative Example 3

The succinic anhydride from example 1 was hydrogenated as a 20% by weight aqueous solution over a Re/Pt/C catalyst analogously to example 1 of DE10009817 A1 (feed rate 100 g/h, temperature 155° C., pressure 220 bar, 20 mol of hydrogen/h, 120 mL of catalyst, tubular reactor, diameter 2 cm, trickle mode). At first, the butane-1,4-diol yield was about 95% with 100% conversion (remainder: butanol, propanol, THF and gamma-butyrolactone). After only 100 h, the conversion decreased to 98% and the butanediol yield was only 90%.

Example 4 (Inventive)

Example 3 was repeated, except that 50 g/h of succinic anhydride was passed at 125° C. over 100 mL of the catalyst (CuO (60% by weight)/$Al_2O_3$ 3 mm tablets) from example 2b at 1.5 bar gauge and 5 standard liters hydrogen/h in liquid phase mode (tubular reactor, oil-heated, diameter 2 cm). The output was collected, dissolved in water according to comparative example 3, and hydrogenated as described therein. The hydrogenation result even after 100 h was the same as at the start (98% butanediol yield, 100% conversion).

We claim:

1. A process for preparing at least one of tetrahydrofuran, butane-1,4-diol, and gamma-butyrolactone, the process comprising the steps of:
    a) fermentatively preparing succinic acid,
    b) converting the succinic acid to succinic anhydride with elimination of water and removal of water,
    c) converting the succinic anhydride to the gas phase,
    d) removing sulfur compounds from the succinic anhydride by passing the gaseous succinic anhydride through a fixed guard bed that absorbs the sulfur compounds,
    e) hydrogenating the gaseous succinic anhydride in the presence of free hydrogen over a metallic catalyst to give the at least one of tetrahydrofuran, butane-1,4-diol, and gamma-butyrolactone.

2. The process according to claim 1, wherein fermentatively preparing succinic acid comprises:
    fermenting from at least one carbon source;
    removing biomass from fermentation broth; and
    converting the biomass to acid form by acidification.

3. The process according to claim 2, further comprising transferring the succinic acid without any further purification steps.

4. The process according to claim 1, wherein step b) is conducted in at least one evaporation apparatus at a pressure in a range from 0.05 to 1 bar and a bottom temperature in a range from 100 to 250° C.

5. The process according to claim 1, wherein step c) is conducted in at least one distillation apparatus at a top pressure in a range from 0.02 to 2 bar and a bottom temperature in a range from 100 to 300° C. and further comprises removing high boilers via a bottom of the at least one distillation apparatus.

6. The process according to claim 5, wherein step c) is conducted at a lower pressure than step b) and further comprises:
    removing water and any low boilers overhead; and
    obtaining the gaseous succinic anhydride via a side draw.

7. The process according to claim 1, wherein step b) and step c) are combined and are conducted in at least one distillation apparatus at a top pressure in a range from 0.02 to 2 bar and a bottom temperature in a range from 100 to 200° C., and wherein the combined step b) and step c) further comprises:
    removing high boilers via a bottom of the at least one distillation apparatus;

removing water overhead; and recovering the gaseous succinic anhydride via a side draw.

8. The process according to claim 1, wherein step e) is conducted at a pressure in a range from 1 to 65 bar and a temperature in a range from 150 to 350° C.

9. The process according to claim 1, wherein a hydrogenation metal in the metallic catalyst is selected from the group consisting of Ru, Re, Co, Cu and mixtures thereof.

10. The process according to claim 1, wherein the metallic catalyst is a supported catalyst in which a support material of the support catalyst comprises at least one of carbon, at least one oxide of B, at least one oxide of Al, at least one oxide of Si, at least one oxide of Ti, at least one oxide of Ze, at least one oxide of La, at least one oxide of Ce, and at least one oxide of Cr.

11. The process according to claim 1, wherein the fixed guard bed includes a sulfur-binding metal selected from the group consisting of Ru, Re, Co, Cu and mixtures thereof.

12. The process according to claim 1, further comprising, after step e), the following step f):

f) distillatively separating water and high boilers from the at least one of tetrahydrofuran, butane-1,4-diol, and gamma-butyrolactone.

13. The process according to claim 12, wherein step f) is conducted in preparation of tetrahydrofuran in at least three distillation columns, wherein f1) in a first distillation column of the least three distillation columns, high boilers are removed in a bottom of the first distillation column and a first tetrahydrofuran/water azeotrope is obtained overhead, f2) the first tetrahydrofuran/water azeotrope from step f1) is separated in a second distillation column of the at least three distillation columns, which is operated at a higher pressure than the first distillation column, into a second tetrahydrofuran/water azeotrope that is removed overhead and tetrahydrofuran that is obtained via a bottom of the second distillation column, f3) the tetrahydrofuran obtained via the bottom in step f2) is freed in a third distillation column of the at least three distillation columns, the third distillation column including high boilers that are discharged via a bottom of the third distillation column.

14. The process according to claim 11, wherein the fixed guard bed has at least one of the same ingredients and the same composition as the metallic catalyst.

15. The process according to claim 13, wherein the second tetrahydrofuran/water azeotrope removed from the second distillation column is recycled into the first distillation column.

* * * * *